US012667989B2

(12) United States Patent
Tellez et al.

(10) Patent No.: US 12,667,989 B2
(45) Date of Patent: Jun. 30, 2026

(54) SURGICAL HAIR CLIPPERS AND VACUUM APPARATUSES INCLUDING SENSING AND FEEDBACK DEVICES

(71) Applicant: CareFusion 2200,Inc., San Diego, CA (US)

(72) Inventors: Isaias Tellez, Kenosha, WI (US); Robert Radford, Skokie, IL (US); Sara Tillman, Vernon Hills, IL (US); Camille A. Sendlak, Arlington Heights, IL (US)

(73) Assignee: CareFusion 2200, Inc., San Diego, CA (US)

(*) Notice: Subject to any disclaimer, the term of this patent is extended or adjusted under 35 U.S.C. 154(b) by 479 days.

(21) Appl. No.: 18/205,276

(22) Filed: Jun. 2, 2023

(65) Prior Publication Data

US 2023/0302672 A1     Sep. 28, 2023

Related U.S. Application Data

(62) Division of application No. 17/022,818, filed on Sep. 16, 2020, now Pat. No. 11,697,215.

(60) Provisional application No. 62/902,532, filed on Sep. 19, 2019.

(51) Int. Cl.
| | |
|---|---|
| *B26B 19/38* | (2006.01) |
| *A61B 17/00* | (2006.01) |
| *B26B 19/06* | (2006.01) |
| *B26B 19/44* | (2006.01) |

(52) U.S. Cl.
CPC ............ *B26B 19/388* (2013.01); *A61B 17/00* (2013.01); *B26B 19/06* (2013.01); *B26B 19/3813* (2013.01); *B26B 19/44* (2013.01)

(58) Field of Classification Search
CPC ... B26B 19/388; B26B 19/06; B26B 19/3813; B26B 19/44; A61B 17/00
USPC ........................................... 15/327.7; 30/133
See application file for complete search history.

(56) References Cited

U.S. PATENT DOCUMENTS

| | | | | |
|---|---|---|---|---|
| 7,159,274 B2 * | 1/2007 | Freidell | ................ | A01K 13/002 |
| | | | | 15/339 |
| 8,359,755 B1 | 1/2013 | Laube | | |
| 9,849,598 B2 | 12/2017 | Damkat et al. | | |
| 10,864,645 B2 | 12/2020 | Magrone | | |
| 2003/0126744 A1 | 7/2003 | Lau et al. | | |

(Continued)

FOREIGN PATENT DOCUMENTS

| | | | | |
|---|---|---|---|---|
| CN | 212072031 U | * | 12/2020 | |
| DE | 19508462 A1 | * | 9/1995 | ............. B26B 19/44 |

*Primary Examiner* — Katina N. Henson
(74) *Attorney, Agent, or Firm* — Dinsmore & Shohl LLP

(57) ABSTRACT

A vacuum apparatus for collecting cut hair includes a housing and a motor located in the housing. A fan is operatively connected to the motor for producing a negative pressure within a filter assembly. A filter assembly includes a filter housing and a filter is located in the filter housing. The filter is configured to move away from an end of the filter housing and increase a storage volume for cut hair within the filter housing. A position sensor is located in the filter housing that is configured to detect the filter. A processor receives a signal from the position sensor when the position sensor detects presence of the filter. The processor uses logic saved in a memory to instruct the motor to increase speed of the motor from an initial speed based on the signal.

14 Claims, 5 Drawing Sheets

(56)  References Cited

U.S. PATENT DOCUMENTS

| | | | |
|---|---|---|---|
| 2006/0230619 A1* | 10/2006 | Williams | ................ B26B 19/44 |
| | | | 30/133 |
| 2014/0345142 A1 | 11/2014 | Damkat et al. | |
| 2015/0183118 A1 | 7/2015 | Roth | |
| 2015/0197016 A1 | 7/2015 | Krenik | |
| 2015/0205279 A1 | 7/2015 | Simeth | |
| 2016/0066542 A1 | 3/2016 | Kearns | |
| 2016/0107323 A1 | 4/2016 | Krans et al. | |
| 2016/0262521 A1 | 9/2016 | Kustra et al. | |
| 2017/0043490 A1 | 2/2017 | Uit De Bulten | |
| 2017/0196640 A1 | 7/2017 | Moeskops et al. | |
| 2017/0291319 A1 | 10/2017 | Van Den Ende et al. | |
| 2017/0325566 A1 | 11/2017 | Franklin et al. | |
| 2017/0361479 A1 | 12/2017 | Magrone | |
| 2019/0015999 A1 | 1/2019 | Darwinkel | |
| 2019/0224869 A1 | 7/2019 | Robinson et al. | |
| 2019/0299432 A1 | 10/2019 | Fuerst et al. | |
| 2019/0299434 A1 | 10/2019 | Fuerst et al. | |
| 2019/0299436 A1 | 10/2019 | Fuellgrabe et al. | |
| 2019/0366569 A1 | 12/2019 | Roth | |
| 2020/0122348 A1 | 4/2020 | Good et al. | |
| 2020/0223077 A1 | 7/2020 | Jaber | |
| 2021/0046663 A1 | 2/2021 | De Boer et al. | |
| 2021/0146562 A1 | 5/2021 | Panagiotopoulou et al. | |

* cited by examiner

SURGICAL HAIR CLIPPERS AND VACUUM APPARATUSES INCLUDING SENSING AND FEEDBACK DEVICES

CROSS-REFERENCE

This application is a division of U.S. patent application Ser. No. 17/022,818, filed Sep. 16, 2020, which claims the benefit of and priority to U.S. Provisional Patent Application No. 62/902,532, filed Sep. 19, 2019, the contents of both which are hereby incorporated herein by reference.

TECHNICAL FIELD

The present disclosure generally relates to surgical hair clippers and associated vacuum apparatuses, and more specifically, to surgical hair clippers and vacuum apparatuses that include sensing and feedback devices and methods of their use.

BACKGROUND

Surgical clippers include blade assemblies that assist with hair removal from the body of a patient in preparation for surgery or other medical procedures for which a skin area of the patient needs to be cleared of hair. Use of surgical clippers by healthcare personnel for hair removal from the skin area may reduce a risk of cuts and abrasions compared to, for example, use of razor blades. It is common to remove hair clippings once they have been cut. One common method of removing hair clippings includes use of an adhesive tape that is pressed against the hair clippings and the skin and then lifted with the hair clippings adhered to the adhesive side of the tape. This method using tape can be inefficient and leave hair behind. In addition, the patient may have an allergic reaction to the adhesive used on the tape.

Vacuum apparatuses have been introduced where a vacuum nozzle is used to pick up hair clippings. Some of these vacuum apparatuses attach to surgical hair clippers to remove hair clippings as they are being cut. These vacuum apparatuses may allow for improper uses of the surgical clippers, such as raking of the blades against the skin and application of too much pressure against the skin. Further, the user may need to visually monitor the hair level in the filter assembly to know when it should be emptied and the vacuum apparatuses may operate at the same level no matter what the level of hair is in the filter assembly.

Accordingly, a need exists for surgical hair clippers and vacuum apparatuses that include sensing and feedback devices and methods of their use.

SUMMARY

According to one embodiment, a surgical hair clipper includes a clipper body and a blade assembly connected to the clipper body. The blade assembly includes a moveable blade configured to reciprocate to remove hair from a skin area and a blade housing that houses the moveable blade. The blade housing has a guide surface that faces the skin area during a hair removal process. A touch sensor is exposed at the guide surface for contact with the skin area during use. A processor receives a signal from the touch sensor when the touch sensor contacts the skin area. The processor uses logic saved in a memory to instruct a feedback device to provide an indication of skin contact between the touch sensor and the skin area.

In another embodiment, a method of using a surgical hair clipper is provided. The method includes contacting a skin area with a guide surface of the surgical hair clipper. The surgical hair clipper includes a clipper body and a blade assembly connected to the clipper body. The blade assembly includes a moveable blade configured to reciprocate to remove hair from the skin area and a blade housing that houses the moveable blade. The blade housing has a guide surface that faces the skin area during a hair removal process. A touch sensor is exposed at the guide surface for contact with the skin area. A processor receives a signal from the touch sensor when the touch sensor contacts the skin area. The processor uses logic saved in a memory to instruct a feedback device to provide an indication of skin contact between the touch sensor and the skin area. The processor instructs the feedback device to provide the indication of skin contact between the touch sensor and the skin area based on a signal from the touch sensor.

In another embodiment, a vacuum apparatus for collecting cut hair includes a housing, a motor located in the housing and a fan operatively connected to the motor for producing a negative pressure within a filter assembly. A filter assembly includes a filter housing and a filter located in the filter housing. The filter is configured to move away from an end of the filter housing and increase a storage volume for cut hair within the filter housing. A position sensor is located in the filter housing that is configured to detect the filter. A processor receives a signal from the position sensor when the position sensor detects presence of the filter. The processor uses logic saved in a memory to instruct the motor to increase speed of the motor from an initial speed based on the signal.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Surgical hair clippers are described herein that include sensing devices that can be used by the surgical hair clippers to provide feedback to a user regarding use of the surgical hair clippers. The sensing devices may be, for example, pressure sensors for detecting pressure of the surgical hair clippers against the skin and/or capacitance sensors for detecting placement of the surgical hair clippers on the skin. The surgical hair clippers may include a processor that can process inputs from the sensing devices and provide feedback to the user, such as yes/no types of feedback using indicators.

Vacuum apparatuses are also described herein that include sensing devices that can be used by the vacuum apparatuses to provide feedback regarding use of the vacuum devices. The sensing devices may be, for example, load sensors and/or position sensors that can provide a signal to a motor controller that is indicative for how much hair resides in a filter assembly of the vacuum apparatuses. The motor control can then control a motor and adjust a power consumption of the vacuum apparatuses based on level of hair in the filter assembly.

Figure 1:
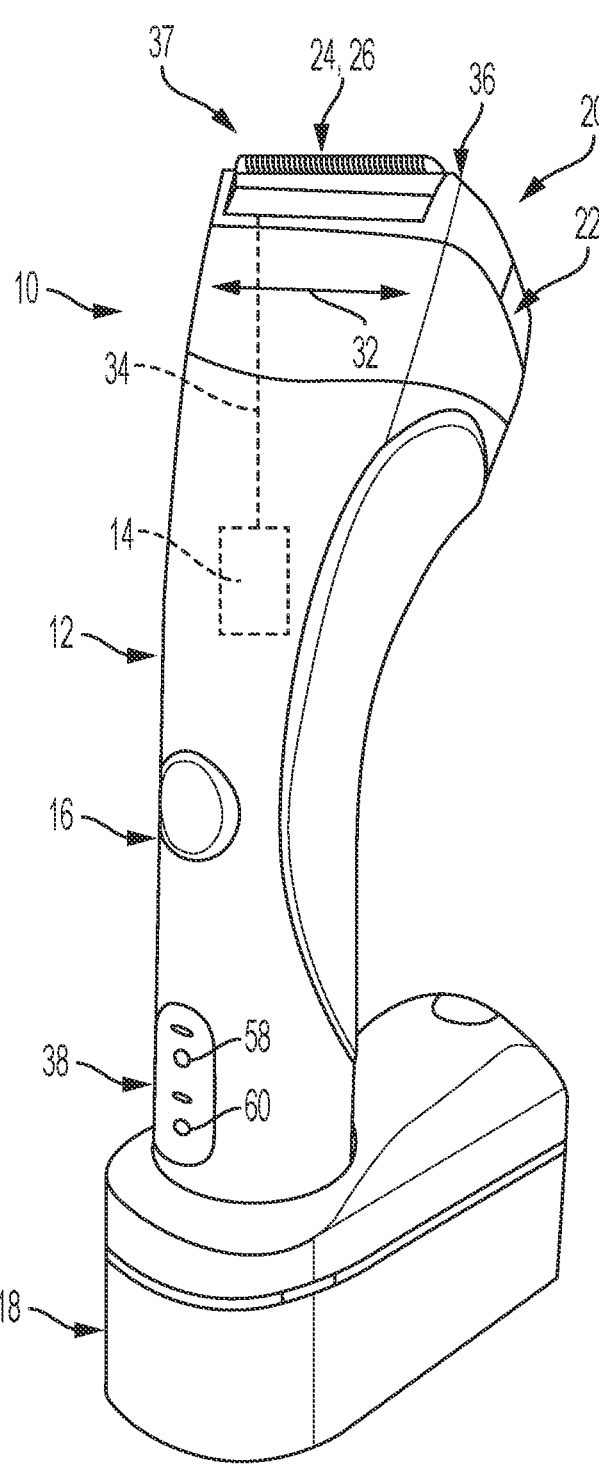
FIG. 1 illustrates a diagrammatic perspective view of a surgical hair clipper, according to one or more embodiments shown and described herein.

Referring to FIG. 1, a surgical hair clipper 10 includes a clipper body 12 that provides a housing for components of the surgical hair clipper, such as a motor (e.g., a rotary motor), which is illustrated schematically by element 14, and a user interface 16 that is used to control operation of the surgical hair clipper 10. The clipper body 12 may further include a rechargeable battery (e.g., a lithium battery) that can be recharged using a charging station 18.

A blade assembly 20 is connected to the clipper body 12. The blade assembly 20 includes a blade housing 22 and a moveable blade 26 that extends outwardly from the blade housing 22. In some embodiments, the blade assembly 20 may be removable from the clipper body 12 and be disposable. In other embodiments, the blade assembly 20 may be a permanent part of the clipper body 12 and may not be intended to be removable without damage to the surgical hair clipper 10. For removable blade assemblies 20, there may different blade assembly types, such as general purpose blade assembly for body hair, a neuro blade assembly for scalp and other thick, course hair and a sensitive blade assembly for perineal/sensitive areas. The blade assemblies may be intended for a single use.

Figure 2:
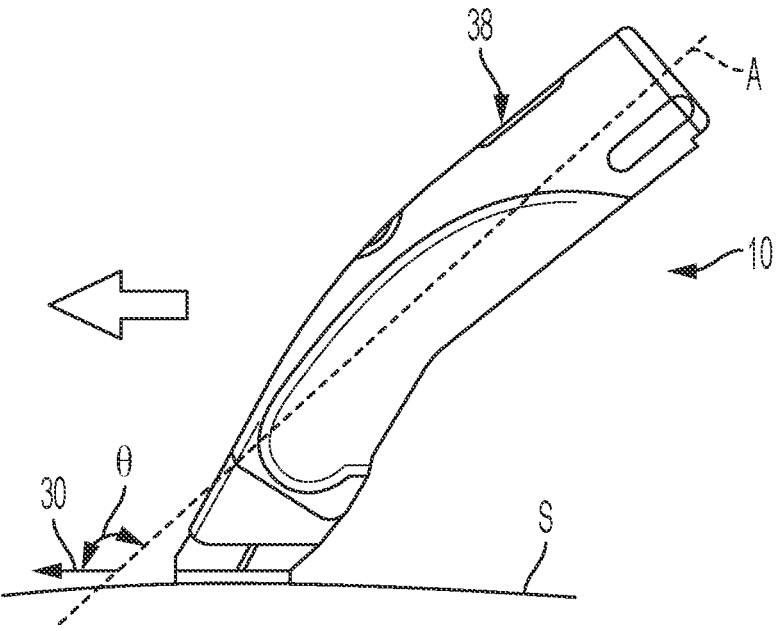
FIG. 2 illustrates a diagrammatic side view of the surgical hair clipper of FIG. 1 in use, according to one or more embodiments shown and described herein.
Figure 3:
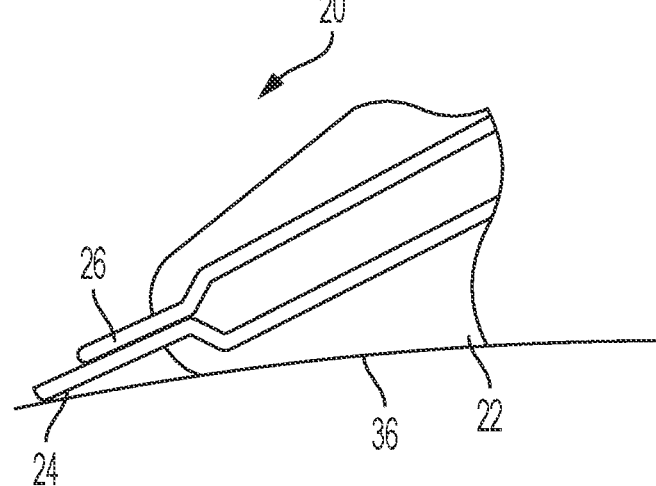
FIG. 3 is a diagrammatic section view of a blade assembly, according to one or more embodiments shown and described herein.

The blade assembly 20 includes the moveable blade 26 and a stationary blade 24 that both extend outwardly from a corner 28 of the blade housing 22 defining a blade cutting direction in the direction of arrow 30 (FIG. 2). Referring also to FIG. 3, the blades 24 and 26 have teeth that provide a comb-like shape across a width of the blades 24 and 26 defining a width direction in the direction of arrow 32 that is perpendicular to the blade cutting direction. The motor 14 reciprocates the moveable blade 26 in the width direction relative to the stationary blade 24 via a linkage 34 in order to cut hair located between the teeth.

A guide surface 36 is located at a skin engagement end 37 of the surgical hair clipper 10. The guide surface 36 faces the skin S during a trimming operation. As can be seen, the guide surface 36 defines a plane that is substantially parallel with the cutting direction 30. In some embodiments, the cutting direction 30 and the guide surface 36 may be at an angle θ (e.g., between about 135 and about 145 degrees) that is oblique to a central axis A that passes through a base portion 38 of the blade housing 22 (FIG. 2).

Figure 4:
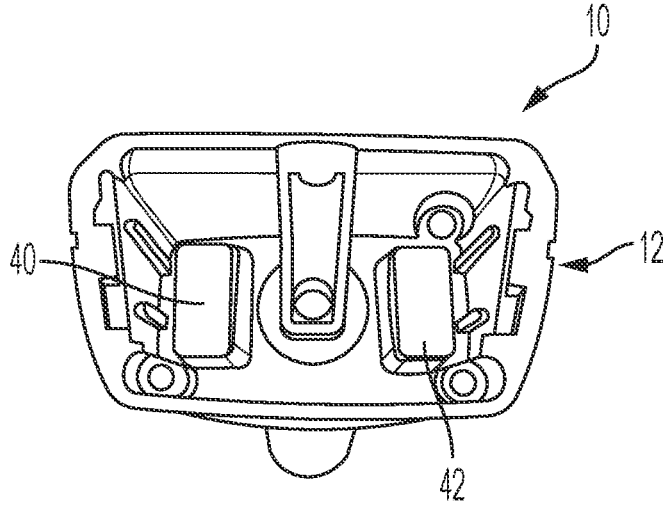
FIG. 4 is an end view of a surgical hair clipper with a blade assembly removed, according to one or more embodiments shown and described herein.
Figure 5:
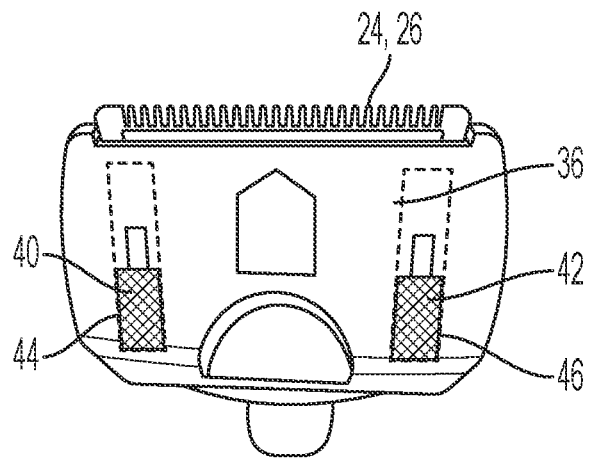
FIG. 5 is an end view of a surgical hair clipper with blade assembly, according to one or more embodiments shown and described herein.

Referring to FIG. 4, an end view of the clipper body 12 of the surgical hair clipper 10 is illustrated without the blades for clarity. A pair of touch sensors 40 and 42 are located in the clipper body 12. The touch sensors 40 and 42 may be, for example, pressure and/or capacitance sensors. The touch sensors 40 and 42 are provided to detect contact with skin during a hair clipping operation. Referring also to FIG. 5 showing the blades 24 and 26 and guide surface 36 connected to the clipper body 12, a pair of openings 44 and 46 may be provided through the guide surface 36 that receive the touch sensors 40 and 42. In some embodiments, the touch sensors 40 and 42 may each have a height to extend at least partially through the openings 44 and 46. In some embodiments, the touch sensors 40 and 42 may be flush with the guide surface 36 to provide a smooth, planar surface that contacts the skin. Thus, the touch sensors 40 and 42 may remain with the surgical hair clipper 10 even when the blades 24 and 26 are removed.

Figure 6:
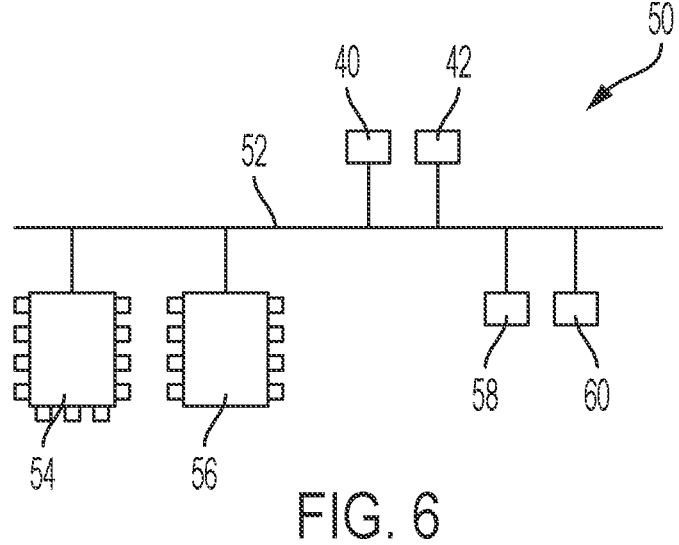
FIG. 6 is a schematic illustration of a control system for the surgical hair clipper of FIG. 1, according to one or more embodiments shown and described herein.

Referring to FIG. 6, a schematic view of a control system 50 for the surgical hair clipper 10 is illustrated. The control system 50 includes a communication path 52 a processor 54, a memory module 56, the touch sensors 40 and 42 and lights 58 and 60. The control system 50 includes the processor 54 communicatively coupled with the memory module 56 over the communication path 52. The processor 54 may include any device capable of executing machine-readable instructions stored on a non-transitory computer-readable medium. The processor 54 may include one or more processors. Accordingly, each processor 54 may include a controller, an integrated circuit, a microchip, a computer, and/or any other computing device.

The memory module 56 is communicatively coupled to the processor 54 over the communication path 52. The memory module 56 may be configured as volatile and/or nonvolatile memory and, as such, may include random access memory (including SRAM, DRAM, and/or other types of RAM), flash memory, secure digital (SD) memory and/or other types of non-transitory computer-readable mediums. The memory module 56 may be configured to store one or more pieces of logic. The memory module 56 may include one or more memory modules.

Embodiments of the present disclosure include logic stored on the memory module 56 that includes machine-readable instructions and/or an algorithm written in any programming language of any generation such as machine language that may be directly executed by the processor 54. Similarly, the logic and/or algorithm may be written in a hardware description language (HDL), such as logic implemented via either a field-programmable gate array (FPGA) configuration or an application-specific integrated circuit (ASIC), and their equivalents. Accordingly, the logic may be implemented in any conventional computer programming language, as pre-programmed hardware elements, and/or as a combination of hardware and software components.

The control system 50 may further include the lights 58 and 60 that are connected to the processor 54 by the communication path 52. The lights 58 and 60 may be, for example, light emitting diodes (LEDs) that are controlled by the processor 54 based on signals from the touch sensors 40 and 42. The lights 58 and 60 may be different colors to provide a user with different indications. For example, a green LED may be used to indicate proper placement and/or pressure on the skin when the processor 54 receives signals from both of the touch sensors 40 and 42. A red LED may be used to indicate improper placement and/or pressure on the skin when the processor 54 receives a signal from only one of the touch sensors 40 or 42. Other outputs may be used, such as a display or speaker.

Figure 7:
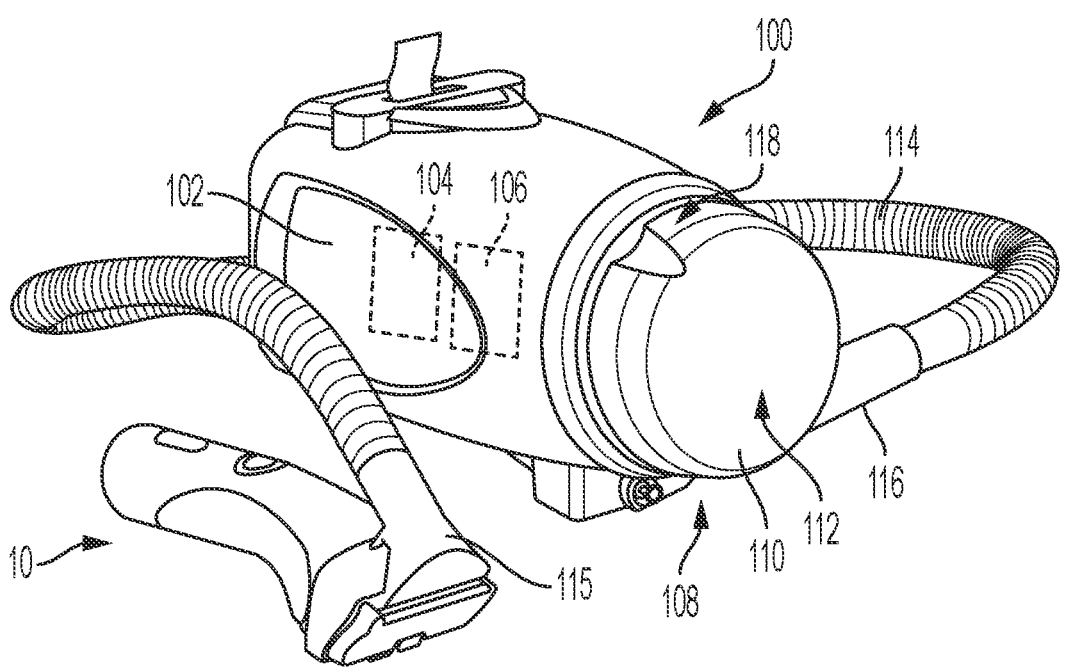
FIG. 7 is a perspective view of a vacuum apparatus, according to one or more embodiments shown and described herein.

While a surgical hair clipper 10 is described above, other surgical preparation devices may include various sensors to improve use and performance, such as a vacuum apparatus 100, as illustrated by FIG. 7. The vacuum apparatus 100 generally includes a housing 102 that houses a motor 104 that is connected to a fan 106 for generating a negative pressure within a filter assembly 108. The filter assembly 108 includes a filter housing 110 that connects to the housing 102 of the vacuum apparatus 100 with a filter 112 located inside the filter housing 110. A vacuum hose 114 is connected to the filter housing 110 by a hose connector 116 that is arranged to tangentially communicate with an interior 118 of the filter housing 110. The vacuum hose 114 may include a nozzle 115 that connects to a surgical hair clipper, such as surgical hair clipper 10 described above.

Figures 8, 9:
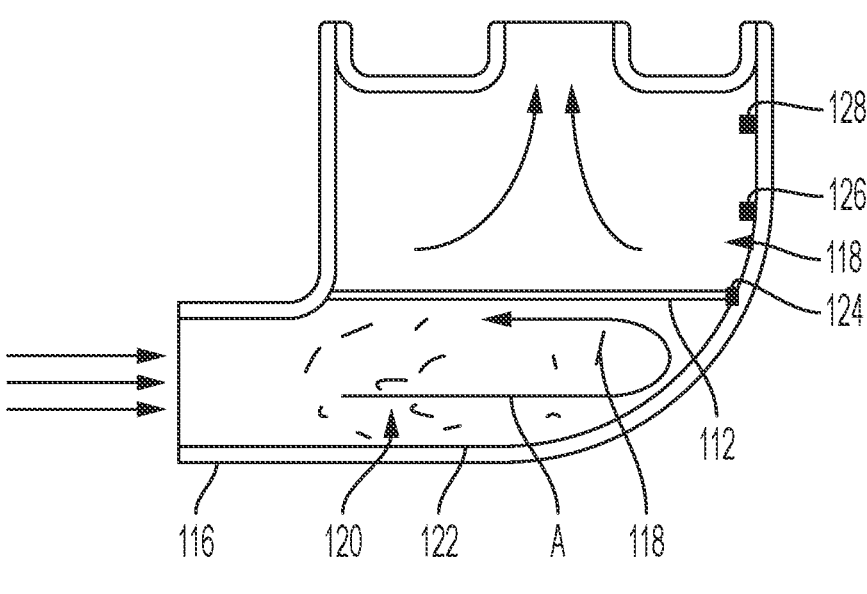
FIG. 8 is a diagrammatic section view of a filter assembly, according to one or more embodiments shown and described herein.
FIG. 9 is a schematic illustration of a control system for the vacuum apparatus of FIG. 7, according to one or more embodiments shown and described herein.

Referring to FIG. 8, the tangential arrangement of the hose connector 116 causes cut hair 118 to move in a spiral, hair collecting vortex in the direction of arrow A. The movement of cut hair 118 in the vortex-like shape can promote improved accumulation of cut hair 118 by the filter 112. As the cut hair 118 accumulates, the filter 112 moves away from end 122 to increase a storage volume 120 for the cut hair 118. As the storage volume 120 increases and fills, suction pressure may decrease for a given amount of motor power.

The filter assembly 108 further includes multiple position sensors 124, 126 and 128 located on an inner surface 129 of a peripheral wall 133 of the filter housing 110. The position sensors 124, 126 and 128 can be any sensor capable of detecting the filter 112 as the filter 112 moves into proximity of the particular position sensor 124, 126 and 128. In some embodiments, the filter 112 may carry a material that is detectable by the position sensors 124, 126 and 128.

The position sensors 124, 126 and 128 may be located at increasing distances from the end 122 representing increases in storage volume 120. For example, position sensor 124 may be located closest to the end 122, position sensor 128 may be located farthest from the end 122 and position sensor 126 may be located between the position sensors 124 and 128. While three position sensors 124, 126 and 128 are illustrated, more or less than three position sensors may be used.

Referring to FIG. 9, a schematic view of a control system 130 for the vacuum apparatus 100 is illustrated. The control system 130 includes a communication path 132 a processor 134, a memory module 136, the position sensors 124, 126 and 128. The control system 130 includes the processor 134 communicatively coupled with the memory module 136 over the communication path 132. As above, the processor 134 may include any device capable of executing machine-readable instructions stored on a non-transitory computer-readable medium. The processor 134 may include one or more processors. Accordingly, each processor 134 may include a controller, an integrated circuit, a microchip, a computer, and/or any other computing device.

The memory module 136 is communicatively coupled to the processor 134 over the communication path 132. The memory module 136 may be configured as volatile and/or nonvolatile memory and, as such, may include random access memory (including SRAM, DRAM, and/or other types of RAM), flash memory, secure digital (SD) memory and/or other types of non-transitory computer-readable mediums. The memory module 136 may be configured to store one or more pieces of logic. The memory module 136 may include one or more memory modules.

Embodiments of the present disclosure include logic stored on the memory module 136 that includes machine-readable instructions and/or an algorithm written in any programming language of any generation such as machine language that may be directly executed by the processor 134. Similarly, the logic and/or algorithm may be written in a hardware description language (HDL), such as logic implemented via either a field-programmable gate array (FPGA) configuration or an application-specific integrated circuit (ASIC), and their equivalents. Accordingly, the logic may be implemented in any conventional computer programming language, as pre-programmed hardware elements, and/or as a combination of hardware and software components.

During operation, the processor 134 uses the machine-readable instructions, which cause the processor 134 to monitor the position sensors 124, 126 and 128. The processor 134 monitors the position sensors 124, 126 and 128 in order to adjust speed of the motor 104 and compensate for the increasing storage volume 120 and related pressure drop. For example, the processor 134 and motor 104 may be considered part of an adjustable speed drive (ASD). In particular, once filter 112 is detected by the position sensor 124, the position sensor 124 may send a signal to the processor 134 indicating presence of the filter 112. In response to the signal from the position sensor 124, the processor 134 may instruct the motor 104 to increase from an initial speed to a first intermediate speed that is higher than the initial speed. Similarly, once filter 112 is detected by the position sensor 126, the position sensor 126 may send a signal to the processor 134 indicating presence of the filter 112. In response to the signal from the position sensor 126, the processor 134 may instruct the motor 104 to increase from the first intermediate speed to a second intermediate speed that is higher than the first intermediate speed. Once filter 112 is detected by the position sensor 128, the position sensor 128 may send a signal to the processor 134 indicating presence of the filter 112. In response to the signal from the position sensor 126, the processor 134 may instruct the motor 104 to again increase from the second intermediate speed to a high speed that is higher than the second intermediate speed. Once the filter assembly 108 is emptied and the filter 112 is not detected by any of the position sensors 124, 126 and 128, the processor 134 may instruct the motor 104 to return to the initial speed. The control system 130 may also include an output, such as a light 140. The light 140 may be activated by the processor 134 when the position sensor 128 detects the filter 112 indicating that the filter assembly 108 is almost full.

The above-described surgical hair clippers include sensing devices that can be used by the surgical hair clippers to provide feedback to a user regarding proper/improper orientation of the blades of the surgical hair clippers. Improper position of the surgical hair clippers can cause toeing of the skin, which can result in nicking. The sensing devices may be any sensor type that can be used to detect contact with and/or pressure against the skin. Multiple sensing devices may be used at different locations of the guide surface.

The above-described vacuum apparatuses also include sensing devices that can detect filling of the filter apparatus through detection of the filter. As the filter apparatus fills, the filter moves to increase a storage volume in the filter apparatus. The position of the filter can be detected using any suitable sensor type. The output from the position sensors can be used to control operation of the motor in order to compensate for decreasing pressure in the filter apparatus. The position of the filter can also be detected to provide feedback to the user, such as when the storage volume approaches a full level.

Clause 1. A surgical hair clipper comprising: a clipper body; a blade assembly connected to the clipper body, the blade assembly comprising a moveable blade configured to reciprocate to remove hair from a skin area and a blade housing that houses the moveable blade, the blade housing having a guide surface that faces the skin area during a hair removal process; a touch sensor that is exposed at the guide surface for contact with the skin area during use; and a processor that receives a signal from the touch sensor when the touch sensor contacts the skin area, wherein the processor instructs a feedback device to provide an indication of skin contact between the touch sensor and the skin area based on the signal.

Clause 2. The surgical hair clipper of clause 1, wherein the touch sensor comprises a capacitance sensor.

Clause 3. The surgical hair clipper of clause 1 or 2, wherein the touch sensor provides a signal to the processor that is indicative of pressure against the skin area.

Clause 4. The surgical hair clipper of any one of clauses 1-3, wherein the touch sensor is connected directly to the clipper body.

Clause 5. The surgical hair clipper of clause 4, wherein the touch sensor has a height to extend at least partially through an opening through the guide surface.

Clause 6. The surgical hair clipper of any one of clauses 1-5 further comprising a pair of touch sensors that are exposed at the guide surface for contact with the skin area during use.

Clause 7. The surgical hair clipper of clause 6, wherein the processor receives a signal from the pair of touch sensors when the pair of touch sensors contact the skin area, wherein the processor uses logic saved in a memory to instruct the feedback device to provide the indication of skin contact between the pair of touch sensors and the skin area.

Clause 8. The surgical hair clipper of clause 7, wherein the processor uses logic saved in memory to instruct another feedback device to provide an indication of lack of skin contact between at least one of the pair of touch sensors and the skin area.

Clause 9. A method of using a surgical hair clipper, the method comprising: contacting a skin area with a guide surface of the surgical hair clipper, the surgical hair clipper comprising: a clipper body; a blade assembly connected to the clipper body, the blade assembly comprising a moveable blade configured to reciprocate to remove hair from the skin area and a blade housing that houses the moveable blade, the blade housing having a guide surface that faces the skin area during a hair removal process; a touch sensor that is exposed at the guide surface for contact with the skin area; and a processor that receives a signal from the touch sensor when the touch sensor contacts the skin area, wherein the processor instructs a feedback device to provide an indication of skin contact between the touch sensor and the skin area based on the signal; and the processor instructing the feedback device to provide the indication of skin contact between the touch sensor and the skin area based on a signal from the touch sensor.

Clause 10. The method of clause 9, wherein the touch sensor comprises a capacitance sensor.

Clause 11. The method of clause 9 or 10 further comprising providing a signal to the processor that is indicative of pressure against the skin area using the touch sensor.

Clause 12. The method of any one of clauses 9-11, wherein the touch sensor is connected directly to the clipper body.

Clause 13. The method of clause 12, wherein the touch sensor has a height to extend at least partially through an opening through the guide surface.

Clause 14. The method of any one of clauses 9-13 further comprising a pair of touch sensors that are exposed at the guide surface for contact with the skin area during use.

Clause 15. The method of clause 14, wherein the processor receives a signal from the pair of touch sensors when the pair of touch sensors contact the skin area, wherein the processor uses logic saved in a memory to instruct the feedback device to provide the indication of skin contact between the pair of touch sensors and the skin area.

Clause 16. The method of clause 15, wherein the processor uses logic saved in memory to instruct another feedback device to provide an indication of lack of skin contact between at least one of the pair of touch sensors and the skin area.

Clause 17. A vacuum apparatus for collecting cut hair comprising: a housing; a motor located in the housing; a fan operatively connected to the motor for producing a negative pressure within a filter assembly; a filter assembly comprising a filter housing and a filter located in the filter housing, the filter configured to move away from an end of the filter housing and increase a storage volume for cut hair within the filter housing; a position sensor located in the filter housing that is configured to detect the filter; and a processor that receives a signal from the position sensor when the position sensor detects presence of the filter, wherein the processor uses logic saved in a memory to instruct the motor to increase speed of the motor from an initial speed based on the signal.

Clause 18. The vacuum apparatus of clause 17, wherein the position sensor is a first position sensor, the vacuum apparatus further comprising a second position sensor located in the filter housing that is configured to detect the filter, wherein the first position sensor is positioned closer to the end of the filter housing than the second position sensor.

Clause 19. The vacuum apparatus of clause 18 further comprising a third position sensor located in the filter housing that is configured to detect the filter, wherein the first position sensor and the second position sensor are positioned closer to the end of the filter housing than the third position sensor.

Clause 20. The vacuum apparatus of clause 19, wherein the processor receives signals from the first position sensor, the second position sensor and the third position sensor when each of the first position sensor, the second position sensor and the third position sensor detects presence of the filter and the processor uses logic saved in the memory to instruct the motor to increase speed of the motor based on which of the first position sensor, the second position sensor and the third position sensor provides the signal.

For the purposes of describing and defining the present disclosure, it is noted that recitations herein of "at least one" component, element, etc., should not be used to create an inference that the alternative use of the articles "a" or "an" should be limited to a single component, element, etc.

It is noted that recitations herein of a component of the present disclosure being "configured" in a particular way, to embody a particular property, or to function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

For the purposes of describing and defining the present disclosure it is noted that the terms "substantially" and "approximately" and "about" are utilized herein to represent the inherent degree of uncertainty that may be attributed to any quantitative comparison, value, measurement, or other representation. The terms "substantially" and "approximately" and "about" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A vacuum apparatus for collecting cut hair comprising:
a housing;
a motor located in the housing;
a fan operatively connected to the motor for producing a negative pressure within a filter assembly;
the filter assembly comprising a filter housing and a filter located in the filter housing, the filter configured to move away from an end of the filter housing and increase a storage volume for cut hair within the filter housing;
a first position sensor located in the filter housing that is configured to detect the filter;
a second position sensor located in the filter housing that is configured to detect the filter, wherein the first position sensor is positioned closer to the end of the filter housing than the second position sensor;
a third position sensor located in the filter housing that is configured to detect the filter, wherein the first position sensor and the second position sensor are positioned closer to the end of the filter housing than the third position sensor; and
a processor that receives signals from the first position sensor, the second position sensor and the third position sensor when each of the first position sensor, the second position sensor and the third position sensor detects presence of the filter and the processor uses logic saved in a memory to instruct the motor to increase or decrease speed of the motor based on which of the first position sensor, the second position sensor and the third position sensor provides the signal.

2. The vacuum apparatus of claim 1 further comprising a hose connector located at the end of the filter housing.

3. The vacuum apparatus of claim 2, wherein the hose connector is configured to draw air into the filter housing in a direction parallel to the filter.

4. The vacuum apparatus of claim 1, wherein the processor uses logic saved in the memory to instruct the motor to increase speed from an initial speed to a first intermediate speed when a first signal is received from the first position sensor.

5. The vacuum apparatus of claim 4, wherein the processor uses logic saved in the memory to instruct the motor to increase speed from the first intermediate speed to a second intermediate speed when a second signal is received from the second position sensor.

6. The vacuum apparatus of claim 5, wherein the processor uses logic saved in the memory to instruct the motor to increase speed from the second intermediate speed to a third intermediate speed when a third signal is received from the third position sensor.

7. The vacuum apparatus of claim 6, wherein the processor uses logic saved in the memory to instruct the motor to decrease speed from the third intermediate speed to the initial speed when no signal is received from the first, second and third position sensors.

8. The vacuum apparatus of claim 6, wherein the processor uses logic saved in the memory to instruct a light to activate when the third signal is received from the third position sensor.

9. A method of controlling operation of a vacuum apparatus, the method comprising:
detecting a first position of a filter within a filter housing using a first position sensor located in the filter housing, the filter configured to move away from an end of the filter housing and increase a storage volume for cut hair within the filter housing, a processor receiving a first signal from the first position sensor when the first position sensor detects presence of the filter;
detecting a second position of the filter within the filter housing using a second position sensor that is positioned farther from the end of the filter housing than the first position sensor;
detecting a third position of the filter within the filter housing using a third position sensor that is positioned farther from the end of the filter housing than the second position sensor; and
wherein the processor receiving signals from the first position sensor, the second position sensor and the third position sensor when each of the first position sensor, the second position sensor and the third position sensor detects presence of the filter and the processor using logic saved in a memory to instruct the motor to increase or decrease speed of the motor based on which of the first position sensor, the second position sensor and the third position sensor provides the signal.

10. The method of claim 9, wherein a hose connector is located at the end of the filter housing.

11. The method of claim 10, wherein the hose connector is configured to draw air into the filter housing in a direction parallel to the filter.

12. The method of claim 9, wherein the processor instructing the motor to increase speed of the motor from an initial speed to a first intermediate speed when the first signal is received from the first position sensor;

the processor instructing the motor to increase speed of the motor from the first intermediate speed to a second intermediate speed when the second signal is received from the second position sensor; and the processor instructing the motor to increase speed of the motor from the second intermediate speed to a third intermediate speed when the third signal is received from the third position sensor.

13. The method of claim 12 further comprising the processor instructing the motor to decrease speed of the motor from the third intermediate speed to the initial speed when no signal is received from the first, second and third position sensors.

14. The method of claim 13 further comprising the processor instructing a light to activate when the third signal is received from the third position sensor.

* * * * *